(12) United States Patent
Huang

(10) Patent No.: US 9,814,619 B2
(45) Date of Patent: Nov. 14, 2017

(54) OPHTHALMOLOGICAL LASER METHOD

(71) Applicant: Cheng-Hao Huang, Orlando, FL (US)

(72) Inventor: Cheng-Hao Huang, Orlando, FL (US)

(73) Assignee: Excelsius Medical, Inc., Orlando, FL (US)

( * ) Notice: Subject to any disclaimer, the term of this patent is extended or adjusted under 35 U.S.C. 154(b) by 209 days.

(21) Appl. No.: 14/489,590

(22) Filed: Sep. 18, 2014

(65) Prior Publication Data

US 2016/0081851 A1    Mar. 24, 2016

(51) Int. Cl.
*A61F 9/008* (2006.01)
*A61F 9/009* (2006.01)

(52) U.S. Cl.
CPC .......... *A61F 9/00804* (2013.01); *A61F 9/009* (2013.01); *A61F 9/00814* (2013.01); *A61F 9/00825* (2013.01); *A61F 9/00827* (2013.01); *A61F 9/00831* (2013.01); *A61F 9/00836* (2013.01); *A61F 2009/0087* (2013.01); *A61F 2009/00872* (2013.01); *A61F 2009/00897* (2013.01)

(58) Field of Classification Search
CPC .................................................. A61F 9/00804
USPC ............................... 606/2–19; 607/80, 88–95
See application file for complete search history.

(56) References Cited

U.S. PATENT DOCUMENTS

| | | | | |
|---|---|---|---|---|
| 4,907,586 A * | 3/1990 | Bille | ....................... | A61F 9/008 606/5 |
| 5,599,340 A * | 2/1997 | Simon | ..................... | A61F 9/008 606/11 |
| 5,971,978 A * | 10/1999 | Mukai | .................. | A61B 18/203 606/11 |
| 7,621,637 B2 | 11/2009 | Rathjen et al. | | |
| 8,585,687 B2 * | 11/2013 | Campbell | ........... | A61F 9/00806 606/4 |
| 2008/0039825 A1* | 2/2008 | Lai | ........................ | A61B 3/107 606/5 |
| 2008/0249517 A1* | 10/2008 | Svanberg | ............. | G02B 6/3809 606/15 |
| 2012/0029492 A1 | 2/2012 | Rathjen | | |

(Continued)

OTHER PUBLICATIONS

Chung, Lu, Automated high-throughput cell microsurgery on-chip, Aug. 19, 2009, Lab on a Chip, p. 2764-2766, DOI: 10.1039/b910703g.*

*Primary Examiner* — Ahmed Farah
*Assistant Examiner* — Jonathan Kuo
(74) *Attorney, Agent, or Firm* — William M. Hobby, III

(57) ABSTRACT

The present invention relates to a femtosecond laser ophthalmological apparatus and method that creates a flap on the cornea for LASIK refractive surgery or for other applications that require removal of corneal and lens tissue at specific locations, such as in corneal transplants, stromal tunnels, corneal lenticular extraction and cataract surgery. The femtosecond laser is transferred from the main cabinet to a hand piece module via a rotating mirror set module. In the hand piece, the femtosecond laser beam is scanned and guided to the patient's eye. The ablation pattern is based on dividing the area of the ablation area into a matrix grid made up of cells. Predetermined ablation pattern is completed in an individual cell before moving on to the next cell until ablation is complete in the entire matrix grid mapped on the ablation area.

7 Claims, 3 Drawing Sheets

(56) References Cited

U.S. PATENT DOCUMENTS

| | | | |
|---|---|---|---|
| 2013/0116672 A1* | 5/2013 | Yee | A61F 9/00821 606/4 |
| 2013/0131653 A1* | 5/2013 | Huang | A61F 9/00827 606/5 |
| 2013/0226157 A1 | 8/2013 | Huang | |
| 2014/0243936 A1* | 8/2014 | Ha | A61N 5/0613 607/90 |

* cited by examiner

OPHTHALMOLOGICAL LASER METHOD

BACKGROUND OF THE INVENTION

The present invention relates to a femtosecond laser ophthalmological apparatus and method that creates a flap on the cornea for LASIK refractive surgery or for other applications that require removal of corneal and lens tissue at specific locations such as in corneal transplants, stromal tunnels, corneal lenticular extraction and cataract surgery.

The use of an excimer laser to modify the shape of the cornea is called Laser Vision Correction (LVC). Currently the most popular method is called LASIK (Laser-Assisted in-situ Keratomileusis) and accounts for approximately 85% of all LVC preformed. Traditionally, during LASIK, the surgeon uses an instrument called a mechanical microkeratome (physical blade) to create a flap on the cornea. However, over the last few years, femtosecond laser has increasingly been used to create a LASIK flap using a series of hundreds of thousands of small laser pulses to create a cleavage plane ("cut") in the cornea.

Femtosecond laser created corneal flaps can offer greater safety, reproducibility, predictability and flexibility over mechanical microkeratome. Furthermore, complications such as buttonhole flaps (in very steep corneas), free caps (in very flat corneas) and irregular flaps that are associated with the mechanical microkeratome are rare with the femtosecond laser. Finally, femtosecond laser systems offer a wide range of other optical-related applications to include corneal transplants, stromal tunnels, corneal lenticular extraction and cataract surgery.

However, several limitations are associated with current femtosecond laser systems:
The overall size of current femtosecond laser systems are much larger than mechanical microkeratome systems. Concurrently, with the exception to Ziemer Ophthalmic AG's Femto LDV systems, current femtosecond laser systems require the patient's eye to be aligned to a fixed laser beam delivery point. These two factors negatively impacts patient and surgeon comfort during surgery. Whereas the corneal flap creation by mechanical microkeratome and subsequent corneal reshaping by an excimer laser system can be done without moving the patient, the size of femtosecond laser systems and fixed delivery require patients to be transferred from one location to another. It is not uncommon for patients to have to move to a separate room to receive corneal reshaping. The femtosecond laser created flaps also increases the surgery time (decreased workflow) as there is often a necessary wait time after laser flap creation (for cavitation gas bubbles to diffuse) before the patient can be moved. This is also a significant reason why most ophthalmology clinics in the world still employ mechanical microkeratome for more efficient workflow.

U.S. Pat. No. 7,621,637 by Rathjen describes an ophthalmological apparatus that Ziemer Ophthalmic AG's Femto LDV series currently utilizes, and it addresses the size, flexibility of delivery and surgery time (small laser spot size for smaller cavitation gas bubbles) issues previously mentioned. Rathjen proposes guiding the laser through a mirror-lens relay arm into a hand piece and attaching a suction unit at the end of the hand piece with a vacuum pump to secure the hand piece on the patient's eye. The system uses a line scanning pattern method of ablation. The line pattern uses a faster scanner to create a pattern and moves the pattern using a slower scanner to cover the necessary area of ablation. The pattern can be moved in a variety of ways to include rotation about a central axis to ablate the necessary area. This method of laser ablation is in contrast to the traditional method used by fixed delivery systems. The fixed delivery systems are able to map the area of the cornea out and have enough laser power and scanning speed to ablate the necessary pattern using a laser spot. This method is not available to a system that needs to guide the laser through an optical unit (mirror-lens relay arm) into a mobile hand piece. There are several disadvantages to Rathjen's method of approach. First, to avoid pattern distortion on the eye created by the translation motor during rotation of the line, the laser pulse line scanning pattern has to be precisely aligned to be perpendicular with the trajectory of the translation motor after passing through the delivery arm. Rathjen compensates with a rotation element to maintain the perpendicular trajectory. This creates a more complex, less reliable and potentially more expensive apparatus. Second, any pattern created by lines will have an inherent width (at a minimum the length of the line) that limits the flexibility of 3D trajectories available. Third, centering the suction ring on the eye while it is attached to the hand piece is cumbersome for surgeons. It requires additional fine movements to align laser spot center and eye center after the suction ring is connected to the eye. Finally, the current design uses a mirror-lens relay optical arm to deliver the laser beam from the main cabinet into the hand piece. Placing lenses in an optical arm amplifies alignment errors and creates a more complex module.

In the present invention an ophthalmological apparatus utilizes a femtosecond laser beam that travels through a rotating mirror set module as opposed to a mirror-lens relay optical arm. Using only mirrors simplifies the optical system's design and operation. The rotating mirror set module is attached to the main cabinet and a hand piece where the laser beam is deflected by a two dimensional XY scanner device into a predetermined pattern of laser pulses. The ablation pattern required is determined by dividing the ablation area into a matrix grid around 12×12 mm centered on the cornea of the eye. The matrix grid is further divided into individual cells and ablation is completed in each individual cell in a predetermined sequence until all cells in the matrix grid have been ablated. This method eliminates the need for compensating optics, rotation elements or trajectory limitations as encountered in the prior art. The suction ring is designed to be aligned and attached to eye center separate from the hand piece. Once the suction ring is fixed on the eye, the hand piece is moved to connect with the suction ring via a slide lock mechanism. This method ensures the suction ring and hand piece are both properly aligned.

SUMMARY OF THE INVENTION

A method of ablating eye tissue using an ophthalmological apparatus includes generating a pulsed laser beam from a femtosecond laser and directing the generated laser beam through a beam expander. A computer controlled electronically activated shutter and a rotating mirror set module are used so that the laser beam enters the hand piece module at normal incidence to its entrance plane. The laser beam is applied to a two dimensional XY scanner in the hand piece module to generate a predetermined scanning pattern of laser pulses (henceforth referred to as "scanning pattern"). The scanning pattern is applied co-axially to a zoom-able scan focusing lens supported by an XYZ translation motor in the hand piece module, and it focuses the scanning pattern onto the patient's eye. The scanning pattern is moved by a XYZ translation motor in a predetermined pattern onto a patient's eye by mapping the area of the cornea into a matrix grid consisting of a plurality of individual cells. The scanning pattern completes ablation in a cell and then moves to complete ablation in the next cell in a predetermined sequence until ablation in all cells of the matrix is complete. The sequence of scanning cells can vary. It is generally most efficient to move from one cell to an adjacent cell until the completion of the scanning in all cells of the matrix. Each cell can be scanned with a random generated scan of laser beam spots on with any scan pattern desired.

BRIEF DESCRIPTION OF THE DRAWINGS

The accompanying drawings, which are included to provide further understanding of the invention, constitute a part of the specification and illustrate the invention together with the description to explain the principles of the invention.

In the drawings.

DETAILED DESCRIPTION OF EXEMPLARY EMBODIMENT

Figure 1:
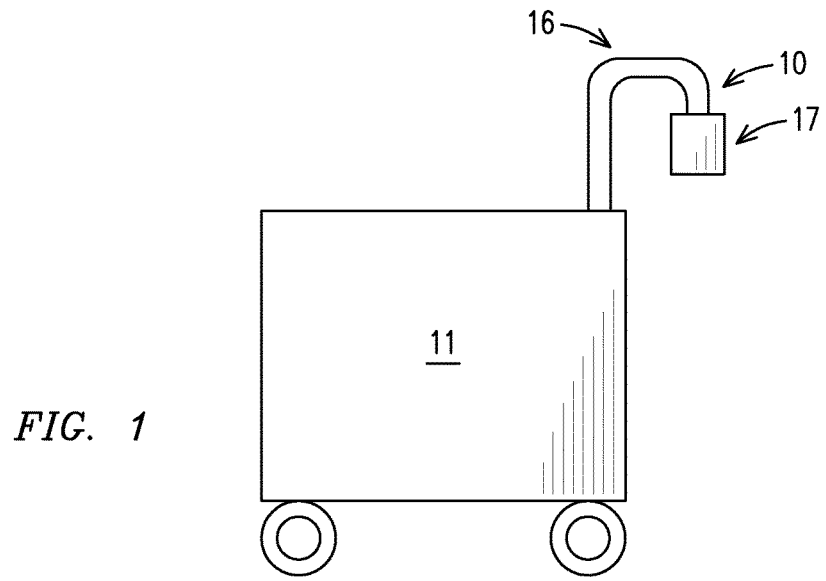
FIG. 1 is a drawing of the exterior of the critical modules of the apparatus and how the modules fit together to form the femtosecond laser ophthalmological surgery apparatus.
Figure 2:
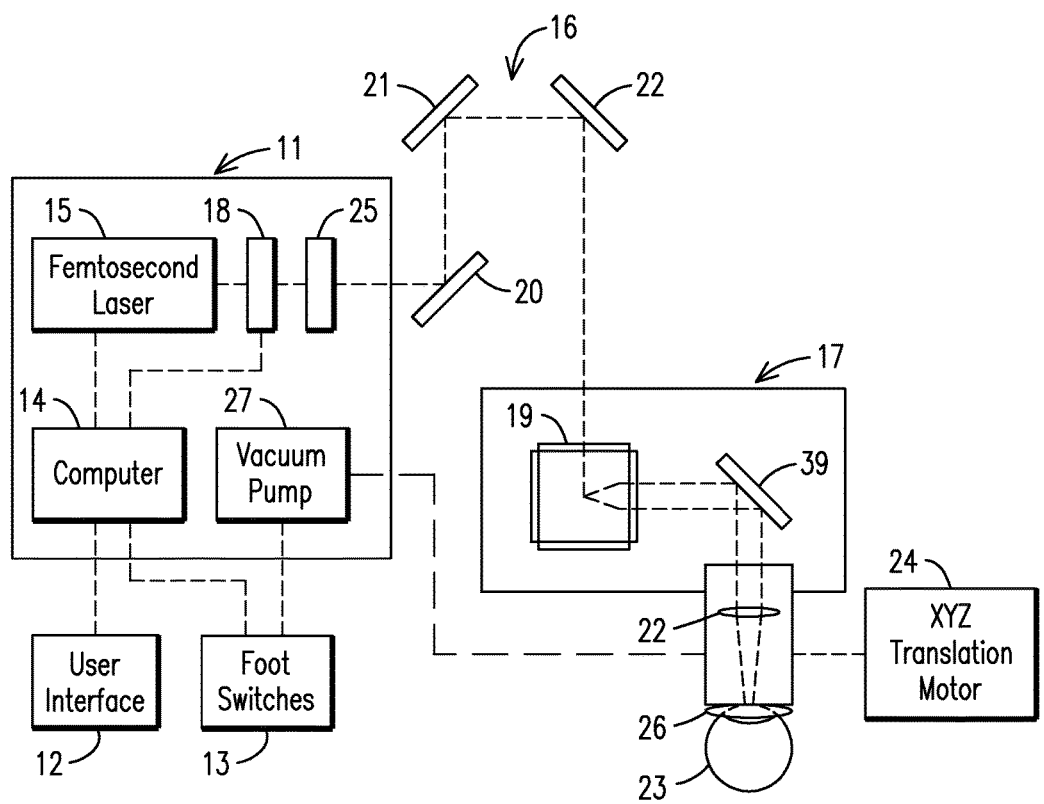
FIG. 2 is a block diagram of a femtosecond laser ophthalmologic surgery apparatus in accordance with the present invention.
Figure 3:
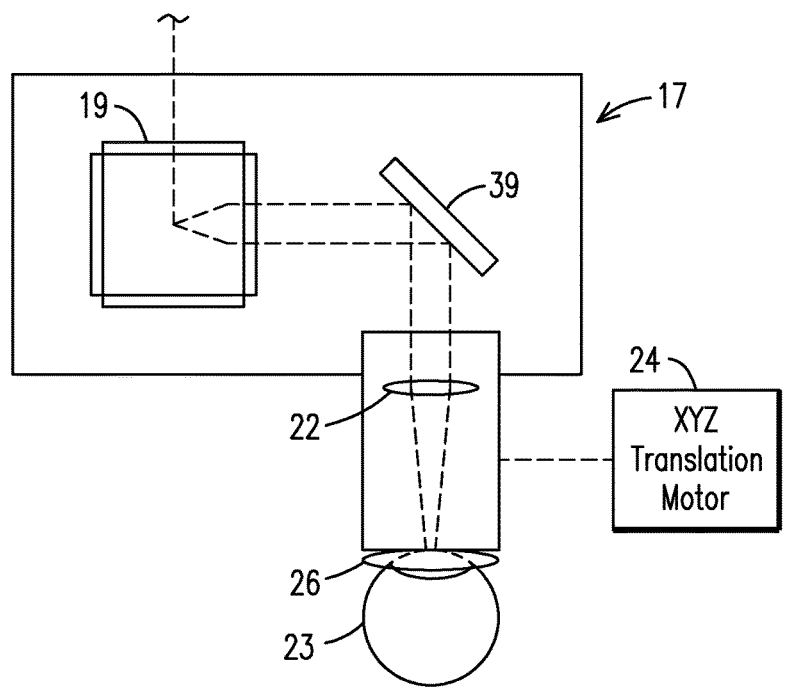
FIG. 3 is a diagrammatic view of the hand piece module of FIGS. 1 and 2 showing the change in femtosecond laser characteristic as it exits the mirror set module, and applied to the two dimensional XY scanner and then focused by the translation motor supported zoom-able scan focusing lens.

The laser ophthalmological surgery apparatus 10 in accordance with the present invention as seen in the drawings, especially as seen in FIGS. 1,2 and 3, includes a user interface 12 connected to a main cabinet 11. A foot switch 13 and the user interface 12 are connected to a computer 14 inside the main cabinet 11. Within the main cabinet 11, laser pulses are generated with a femtosecond laser 15 that is guided through an attached rotating mirror set module 16. The ophthalmological apparatus 10 has the main cabinet 11 and a hand piece module 17 connected to either end of the rotating mirror set module 16. A laser beam expander 18 is positioned in the main cabinet 11 to enlarge the laser beam spot size before it is directed through the rotating mirror set module 16. The laser beam passes through the rotating mirror set module 16 having mirrors 20, 21, and 22, but can have more than three mirrors as desired, and into the hand piece module 17 at normal incidence to the two dimensional XY scanner 19. The two dimensional XY scanner 19 deflects the laser beam to create a scanning pattern of laser pulses. Inside the hand piece, a zoom-able scan focusing lens 22 is used to reduce the laser beam spot size. The lens is supported by a XYZ translation motor 24 in the hand piece module 17 that is used to move the scanning pattern according to a predetermined sequence onto the patient's eye 23.

Figure 5:
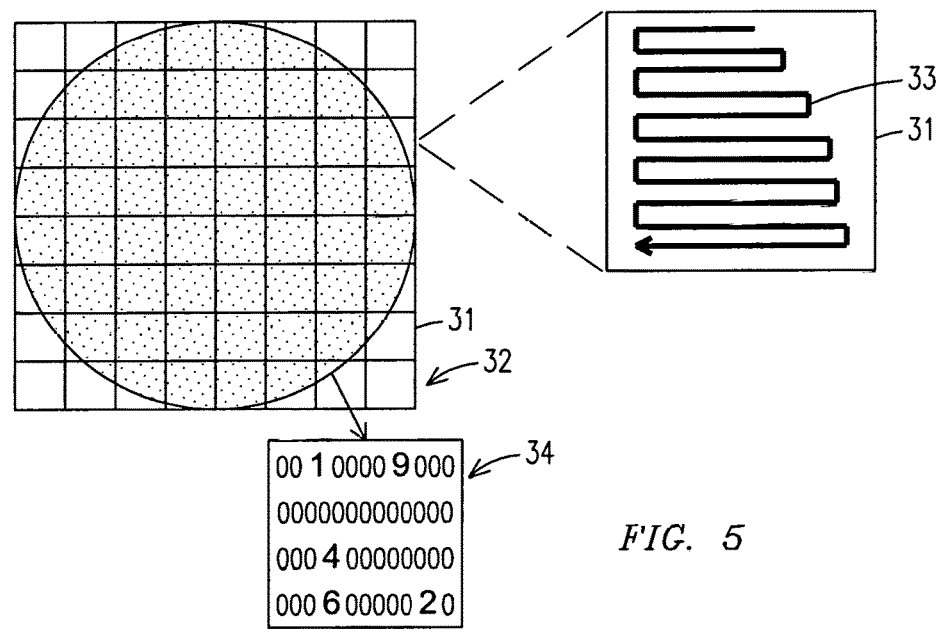
FIG. 5 is the area of a cornea mapped as a matrix grid consisting of individual cells and the scanning pattern in each individual cell of the matrix.
Figure 6:
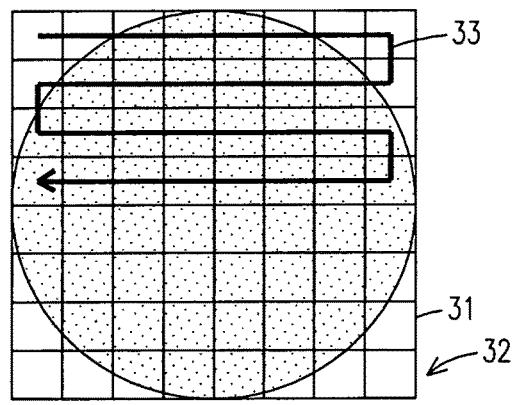
FIG. 6 is a diagram of a horizontal serpentine sequence to scan from cell to cell of the matrix.
Figure 7:
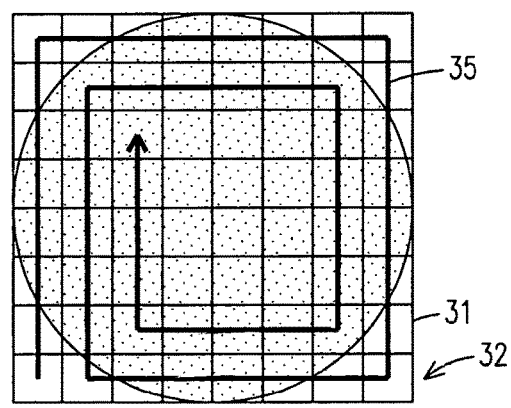
FIG. 7 is a diagram of a spiral sequence to scan from cell to cell of the matrix.

Following the light path in greater detail, the light pulse generator is a femtosecond laser 15, which may have a pulse width less than 1000 femtoseconds and a pulse repetition rate greater than 10 KHz. The laser beam spot size is enlarged by a beam expander 18 and is then blocked by a shutter 25 until the foot switch 13 is depressed. While the foot switch 13 is depressed, the beam is allowed to continue through the rotating mirror set module 16 and into the hand piece module 17 as shown in FIG. 2. Inside the hand piece module 17, the laser beam is deflected by the two dimensional XY scanner 19 into a predetermined scanning pattern and deflected by a mirror 39 to ablate the cornea based on a matrix grid sequence. The cornea is divided into a multitude of individual cells, as seen in FIGS. 5, 6 and 7, that make up a matrix grid that covers the entire area of the cornea. The laser will sequentially complete scanning in one cell before moving on to the next cell and continue doing so until scanning in all cells of the matrix is complete. Each cell 31 in the matrix can be scanned with a random generated scan of laser beam spots 34 to fully scan the cell 31 or can be scanned with any scan pattern desired. The scanning pattern may have a laser pulse repetition rate up to 2 MHz.

Figure 4:
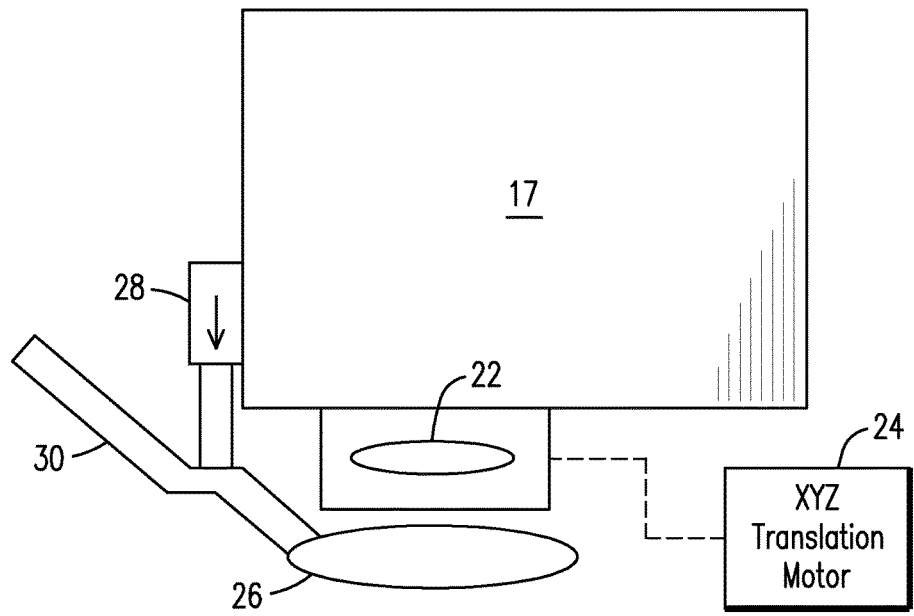
FIG. 4 is a side diagrammatic view of the hand piece module and the slide lock mechanism of the suction ring.

Inside the hand piece 17, as more clearly seen in FIGS. 3 and 4, a compact, low F-number (high numeric aperture) zoom-able scan focusing lens 22 is mounted on an XYZ translation motor 24 to reduce the spot size of the laser beam to less than 3 microns. The translation motor 24 supports the zoom-able scan focusing lens 22 and has a smaller size and higher focusing capability than the F-theta lens that is currently most commonly used in femtosecond ophthalmic systems. The higher focusing capability generates a smaller laser beam spot size that reduces the required energy based on the same energy density. Reduced energy levels form smaller cavitation bubbles and are absorbed faster by the surrounding tissue. This also means the acoustic wave impact caused by the photo disruption is reduced. Furthermore, the smaller lens size can be incorporated into a smaller hand piece module that makes it easier to integrate with existing UV laser ophthalmic apparatus for LASIK.

The hand piece 17 is attached to the eye via a clear disposable suction ring 26 as shown in FIG. 4. The disposable suction ring 26 is placed on the eye 23 and secured using the low pressure created and maintained by a vacuum pump 27. The hand piece 17 is connected to the detachable disposable suction ring 26 by a slide lock mechanism. The laser beam passes through the disposable suction ring 26 onto the cornea of the eye 23. The suction ring 26 is placed on the eye 23 and aligned using a microscope. Once aligned, the hand piece is manually pushed into the proper position as dictated by the suction ring 26. Since the suction ring 26 is completely clear when viewed under the microscope, alignment is easily performed. A handle 30 has the vacuum line connected thereinto and has a slidelock mechanism 28 as seen in FIG. 4.

It will be clear at this point that a key point of the present invention is dividing a scanning area into a matrix grid 32 of cells 31 and then completing the scanning of each individual cell 31 before moving on to the next cell 31 in a sequence 33. Each cell 31 can be scanned with a random generated scan of beam spots 34 or with any other scan pattern within each cell 31 to cover the entire cell, as shown for one cell in FIG. 5, before moving to the next cell. The cells 31 are placed in a matrix grid 32 and then each cell 31 is scanned with the laser beam before moving in any pattern desired, such as a random generated scan 34, within the cell before going to the next cell 31. In FIG. 6 the area of the cornea mapped as a matrix grid 32 consist of individual cells 31 and a horizontal snake or serpentine scanning path or sequence 33 used to cover the grid as each individual cell of the matrix is scanned along a horizontal axis. Each cell is fully scanned before scanning the next cell in a horizontal row of cells one at a time until the scanning of the grid is complete. FIG. 6 shows the sequence 33 of scanning from cell to cell with the scanning being completed from one cell 31 to an adjacent cell 31 for all cells in a row of the matrix before scanning the next row until all scanning is complete. FIG. 7 shows a spiral sequence 35 for scanning each cell 31 in the outer most ring of cells 31 and continues until all cells are scanned.

The present ophthalmological apparatus 10 can be seen as having a main cabinet 11 and a hand piece module 17 connected to the main cabinet 11 by a rotating mirror set module 16 having a plurality of mirrors 20, 21, and 22. A femtosecond laser source 15 is positioned in the main cabinet 11. The laser beam output of laser pulses is manually activated by a shutter 25 mounted between the femtosecond laser source 15 and the rotating mirror set module 16. A laser beam expander 18 is positioned to enlarge the femtosecond laser beam laser pulses while a two dimensional XY scanner 19 laser scanner is positioned in the hand piece module 17 for scanning the laser beam into a predetermined pattern of laser pulses. An XYZ translation motor 24 is located in the hand piece 17 and has a focusing lens 22 mounted thereto. The XYZ translation motor 24 is positioned for receiving a predetermined pattern of laser pulses from the laser scanner 19 which scans the predetermined pattern of laser pulses onto the patient's eye 23 to complete the ablation in an individual cell 31 of the matrix grid 32. A detachable suction ring 26 is placed onto the patient's eye 23 and then attached to the hand piece 17 with a slide lock mechanism 28 for scanning the eye 23. The ablation area is mapped as a matrix grid 32 consisting of a multitude of individual cells 31 and ablation of an individual cell 31 of the matrix grid 32 are completed one by one until all cells 31 of the mapped matrix grid 32 of the patient's eye 23 have been ablated.

The method of ablating eye tissue in accordance with the present invention includes the mapping of an ablation area for a patient's eye as a matrix grid 32 consisting of a multitude of individual cells 31 and then generating a laser beam of laser spots from a femtosecond laser source 15. The generated laser beam from the femtosecond laser source 15 is then directed through a rotating mirror set module 16 so the laser beam enters a hand piece module 17 at normal incidence to its entrance plane. The generated laser beam is applied to a laser scanner 19 in the hand piece 17 to generate a predetermined scanning pattern of laser pulses. An XYZ translation motor 24 is then selected which supports a zoom-able scan focusing lens 22. The predetermined scanning pattern of laser pulses generated by the laser scanner is then applied onto the translation motor 24 supported zoom-able scan focusing lens 22 which focuses the predetermined scanning pattern of laser pulses onto a patient's eye 23 and scanning the predetermined pattern of laser pulses onto the patient's eye 23 to complete the ablation in an individual cell 31. The ablation of an individual cell 31 of a matrix 32 is then completed one cell at a time until all cells 31 of the mapped matrix 32 of the patient's eye 23 has been ablated. The matrix grid 32 ablation sequence may be a serpentine like sequence 33 of individual cells as shown in FIG. 6 or may be a spiral sequence 36 as shown in FIG. 7 of individual cells 31. The process may include selecting an XYZ translation motor 24 supported zoom-able scan focusing lens 22 in an adjustable hand piece module 17. The process may also include mounting the femtosecond laser source 15 in a main cabinet 11 and the laser scanner 19 in the hand piece module 17 connected to the main cabinet 11 by a rotating mirror set module 16. Other steps in the process may include selecting a beam expander 18 and applying the femtosecond laser 15 to the beam expander 18 in the main cabinet 11 to enlarge the femtosecond laser beam spot and selecting a hand piece 17 having a detachable suction ring 26 connected by a slide lock mechanism 28 for attaching the hand piece 17 to a patient's eye 23.

It should be clear at this time that a femtosecond laser eye surgery method and apparatus has been described which highlights the advantages of delivering a laser beam remotely using a rotating mirror set module (as opposed to mirrors and lenses) into a hand piece module and using a matrix grid of cells to sequentially organize and ablate tissue. However, it should be clear that the present invention is not to be considered as limited to the forms shown which are to be considered illustrative rather than restrictive.

I claim:

1. A method of ablating eye tissue comprising the steps of:
   mapping an ablation area as a matrix consisting of a plurality of individual cells;
   generating a laser beam from a femtosecond laser source;
   directing the generated laser beam through a rotating mirror set module so that the laser beam enters a hand piece module at normal incidence to its entrance plane;
   applying the generated laser beam to a laser scanner in the hand piece to generate a predetermined scanning pattern of laser pulses;
   selecting an XYZ translation motor supported zoom-able scan focusing lens;
   applying the predetermined scanning pattern of laser pulses generated by said laser scanner onto said translation motor supported zoom-able scan focusing lens;
   focusing the predetermined scanning pattern of laser pulses onto a patient's eye; and
   ablating each cell of a predetermined pattern of cells in said matrix plurality of cells with a randomly generated beam of laser pulses from said generated laser beam to complete the random ablation of one individual cell in said predetermined pattern of cells before proceeding to the next cell in said predetermined pattern of cells in said matrix plurality of cells;
   whereby ablation of a patient's eye tissue is done by randomly ablating one cell at a time of a matrix of cells along a predetermined path within the matrix of cells.

2. The method of ablating eye tissue in accordance with claim 1 in which the ablation of said matrix of cells randomly ablates one cell at a time going from one cell to the next in a serpentine pattern through said matrix of cells.

3. The method of ablating eye tissue in accordance with claim 1 in which the ablation of said matrix of cells randomly ablates one cell at a time going from one cell to the next in a spiral pattern through said matrix of cells.

4. The method of ablating eye tissue in accordance with claim 1 including the step of mounting said selected XYZ translation motor supported zoom-able scan focusing lens in an adjustable hand piece module.

5. The method of ablating eye tissue in accordance with claim 1 including the step of mounting said femtosecond laser source in a main cabinet and said laser scanner in a hand piece module connected to the main cabinet by a rotating mirror set module.

6. The method of ablating eye tissue in accordance with claim 1 including the step of selecting a beam expander and applying the femtosecond laser to the beam expander in a main cabinet to enlarge the femtosecond laser beam spot size.

7. The method of ablating eye tissue in accordance with claim 1 including the step of selecting a hand piece having a detachable suction ring connected by a slide lock mechanism for attaching the hand piece to a patient's eye.

\* \* \* \* \*